United States Patent [19]
Cohen et al.

[11] Patent Number: 5,981,496
[45] Date of Patent: Nov. 9, 1999

[54] α-PYRONES FOR TREATING α-PYRONE RESPONSIVE STATES

[75] Inventors: Seth Cohen, Westwood; Zhi-Dong Jiang, Burlington, both of Mass.

[73] Assignee: Millennium Pharmaceutical, Inc., Cambridge, Mass.

[21] Appl. No.: 08/933,777

[22] Filed: Sep. 19, 1997

[51] Int. Cl.$^6$ .................. A61K 31/35; C07D 309/36; C07D 309/40

[52] U.S. Cl. .................. 514/25; 514/27; 536/4.1; 549/200; 549/356; 549/416; 549/423; 549/13; 549/62; 549/64; 549/66

[58] Field of Search .................. 536/4.1; 514/25; 514/27; 549/416, 423, 62, 64, 66

[56] References Cited

U.S. PATENT DOCUMENTS

| | | | |
|---|---|---|---|
| 3,973,945 | 8/1976 | Fujino et al. | 71/88 |
| 4,992,271 | 2/1991 | Fernandes et al. | 424/85.2 |
| 5,314,685 | 5/1994 | Praveen et al. | 424/401 |

FOREIGN PATENT DOCUMENTS

WO 88/10258  12/1988  WIPO.

OTHER PUBLICATIONS

Evidente et al., (CA 121:276292, abstract of Nat. Toxins (1994), 2(1), 4–13.

Visconti et al. (CA 121:200529, abstract of J. Nat. Prod. (1994), 57(6), 695–9.

Brienholt et al. (CA 120:52828, abstract of WO 9322444), 1993.

Berge, S.M., et al., "Pharmaceutical Salts", *J. Pharm. Sci.*, 66:1–19 (1977).

Poulton, G.A., and Cyr, T.D., "Pyrones. VI. The total synthesis of phacidin", *Can. J. Chem.*, 58:2158–2160 (1980).

Groutas, W.C., et al., "Substituted 2–Pyrones, 2–Pyridones, and Other Congeners of Elasnin as Potential Agents for the Treatment of Chronic Obstructive Lung Diseases", *Journal of Medicinal Chemistry*, 28:1106–1109 (1985).

Wang, C.-S., "Structure and Chemistry of 4–Hydroxy–6–methyl–2–pyridone", *J. Heterocycl. Chem.*, 7:389–392 (1970).

Spencer, R.W., et al., "Inhibition of Human Leukocyte Elastase, Porcine Pancreatic Elastase, and Chymotrypsin by Elasnin and Other 4–Hydroxy–2–pyrones", *J. Med. Chem.*, 28:1828–1832 (1985).

Groutas, W.C., et al., "Specific inhibition of human leukocyte elastase by substituted alpha–pyrones", *Experientia*, 40:361–362 (1984).

Omura, S., et al., "Elasnin, A New Human Granulocyte Elastase Inhibitor Produced By A Strain of Streptomyces", *Biochemical and Biophysical Research Communications*, 83:704–709 (1978).

Banfalvi, G. and Sarkar, N., "Origin and Degradation of the RNA Primers at the 5' Termini of Nascent DNA Chains in *Bacillus subtilis*", *J. Mol. Biol.* 186:275–282 (1985).

Higgins, N.P., et al., "Bacteriophase Mu DNA Replication in Vitro", *The Journal of Biological Chemistry*, 258:4293–4297 (1983).

Dunn, J.J. and Studier, F.W., "Nucleotide Sequence from the Genetic Left End of Bacteriophase T7 DNA to the Beginning of Gene 4", *J. Mol. Biol.* 148:303–330 (1981).

Munson, B.R., et al., "Segregation of Relaxed Replicated Dimers When DNA Ligase and DNA Polymerase I Are Limited during oriC–Specific DNA Replication", *Journal of Bacteriology*, 171:3803–3809 (1989).

Ciarrocchi, G., et al., "Correlation between anthracycline structure and human DNA ligase inhibition", *Biochem. J.* 279:141–146 (1991).

Yang, S–W, et al., "Identification of a specific inhibitor for DNA ligase I in human cells", *Proc. Natl. Acad. Sci. USA*, 89:2227–2231 (1992).

David, J–C, et al., "Inhibition of DNA Ligase from Human Thymocytes and Normal or Leukemic Lymphocytes by Antileukemic Drugs", *Cancer Research*, 45:2177–2183 (1985).

Tan, G.T., et al., "Natural–product inhibitors of human DNA ligase I", *Biochem. J.*, 314:993–1000 (1996).

Barnes, D.E., et al., "Human DNA ligase I cDNA: Cloning and functional expression in *Saccharomyces cerevisiae*", *Proc. Natl. Acad. Sci. USA*, 87:6679–6683 (1990).

Shuman, S. and Schwer, B., "RNA capping enzyme and DNA ligase: a superfamily of covalent nucleotidyl transferases", *Molecular Microbiology*, 17(3):405–410 (1995).

Kodama, K–i, et al., "In vitro mutagenesis and functional expression in *Escherichia coli* of a cDNA encoding the catalytic domain of human DNA ligase I", *Nucleic Acids Research*, 19:6093–6099 (1991).

Subramanya, H.S., et al., "Crystal Structure of an ATP–Dependent DNA Ligase from Bacteriophase T7", *Cell*, 85:607–615 (1996).

*Primary Examiner*—Jose G. Dees
*Assistant Examiner*—Sabiha N. Qazi
*Attorney, Agent, or Firm*—Lahive & Cockfield, LLP; Elizabeth A. Hanley

[57] ABSTRACT

Novel α-pyrones are described. The α-pyrones are useful in a method for controlling α-pyrone responsive states in a mammal. The method includes administering to a mammal a therapeutically effective amount of an α-pyrone such that control of α-pyrone responsive states in a mammal occurs. α-Pyrone responsive states can be associated with undesirable cell proliferation such as bacteria or cancer. Packaged pharmaceuticals and pharmaceutical compositions including the novel α-pyrones are also described.

8 Claims, No Drawings

α-PYRONES FOR TREATING α-PYRONE RESPONSIVE STATES

BACKGROUND

Methods and compositions for inhibiting the growth of aberrant cells are desirable in a variety of situations, for example, to suppress the growth of pathogenic microorganisms infecting a host subject or to suppress the growth of cancer cells in a host subject. Various types of agents for inhibiting aberrant cell growth have been developed. For example, to inhibit the growth of bacterial cells, natural antibiotics (chemical substances produced by microorganisms such as bacteria, fungi and actinomycetes) have been identified and characterized. Synthetic antibiotics, such as sulfonamides and quinolones, have also been developed. Growth of mammalian cells (e.g., malignant cells) can be inhibited by a variety of toxic compounds or therapies, such as nucleoside analogs, metal-containing drugs or radiation treatment, which interfere with normal cellular metabolism.

Transformation, or malignant transformation, of cells results in changes in their growth characteristics and can cause them to form tumors in the infected animals. For example, aberrant cells can be associated with changes in growth control, cell morphology, membrane characteristics, protein secretion and gene expression. Although aberrant cell transformation can occur spontaneously, it can be caused by a chemical or irradiation or may result from infection by a tumor virus. Little is known about the underlying molecular events.

DNA ligase is an enzyme which is involved in DNA replication, repair and recombination. DNA ligase acts by joining single and doubled stranded DNA with the formation of phosphodiesters bonds. For example, eurkaryotic DNA ligases react with ATP, thereby forming covalent enzyme-AMP intermediates. The enzymes then transfer the AMP group to the 5' end of the DNA to complete the joining reaction. DNA ligase joining activity has been implicated in the proliferation of aberrant cell growth, such as in bacteria and in mammalian cancer.

Although known growth inhibitory agents have been used successfully to suppress the growth of cells to ameliorate certain disease states, there are limitations to their use. For example, the widespread use of antibiotics has increasingly led to the problem of resistant pathogens whose growth can no longer be inhibited by known antibiotics. The appearance of multi-drug resistant pathogens has prompted a search for new classes of antibiotics which are structurally and/or functionally different from existing drugs. Drugs having new mechanisms of action could be effective against resistant microorganisms, where conventional drugs can no longer be used. Chemotherapeutic agents for suppressing the growth of mammalian cells (e.g., malignant cells) also have limitations. Chemotherapeutic agents often have deleterious side effects and/or show only limited efficacy.

SUMMARY OF THE INVENTION

The present invention is based, at least in part, on the discovery that certain α-pyrones can be used to treat an α-pyrone responsive state. Examples of such states include undesirable cell proliferation, bacterial infection, or cancer. In a preferred composition and method, the α-pyrone includes a sugar moiety as a solubilizing moiety and an alkyl ester as a cell penetrating moiety.

The present invention provides methods for controlling undesirable cell proliferation in a mammal by administering to the mammal a therapeutically effective amount of an α-pyrone, such that control of undesirable cell proliferation in the mammal occurs.

The present invention also provides methods for controlling a bacterial infection in a mammal by administering to a mammal a therapeutically effective amount of an α-pyrone, such that control of a bacterial infection in the mammal occurs.

The present invention further provides methods for treating cancer in a mammal by administering to the mammal a therapeutically effective amount of an α-pyrone, such that treatment of the cancer in the mammal occurs.

The present invention provides methods for treating diseases characterized by aberrant DNA ligase joining activity in a mammal by administering to the mammal a therapeutically effective amount of an α-pyrone, such that aberrant DNA ligase joining activity in the mammal is treated. The DNA ligase joining activity can be associated with undesirable cell proliferation, such as bacterial or cancer proliferation.

The present invention provides new and useful compounds, α-pyrones, and combinations of such compounds. Subgenuses of α-pyrones that are included in this invention are described below. It should be understood that combinations of α-pyrones within each of these subgenuses are intended to be part of this invention. It should also be understood that such combinations of α-pyrones can be used within the pharmaceutical compositions, packaged pharmaceuticals and methods described herein.

The first subgenus of this invention has the formula

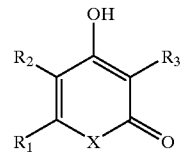

and pharmaceutically acceptable salts or esters thereof. X is O, S, N or P. $R_1$ or $R_2$ are each independently a hydrogen atom or a cell penetrating moiety and $R_3$ is a solubilizing moiety. Preferably, $R_1$ is a cell penetrating moiety, such as a substituted or unsubstituted alkyl ester group and $R_3$ is a solubilizing moiety, such as a sugar.

The invention also provides new and useful compounds, α-pyrones, having the formula

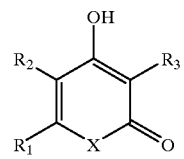

and pharmaceutically acceptable salts or esters thereof. X is O, S, N or P. $R_1$ or $R_2$ are each independently a hydrogen atom or a lipophilic solubilizer and $R_3$ is a solubilizing moiety. Preferably, $R_1$ is a lipophilic solubilizer, such as a substituted or unsubstituted alkyl ester group and $R_3$ is a solubilizing moiety, such as a sugar.

The invention further provides new and useful compounds, such as α-pyrones, having the formula:

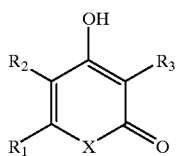

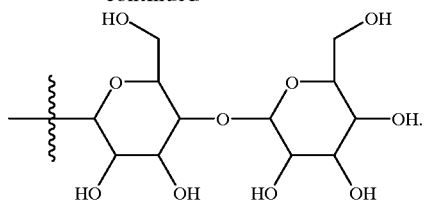

and pharmaceutically acceptable salts or esters thereof. X is O, S, N or P. $R_1$ or $R_2$ are each independently a hydrogen atom or a hydrophobic moiety and $R_3$ is a solubilizing moiety. In one embodiment, $R_1$ is a hydrophobic moiety, $R_2$ is a hydrogen atom and $R_3$ is a hydrophilic moiety. In a preferred embodiment, X is O, the hydrophobic moiety is the alkyl ester group

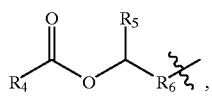

wherein $R_4$ is

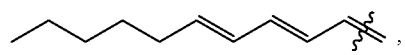

$R_5$ is a methyl group, $R_6$ is a covalent bond to the α-pyrone ring and the hydrophilic moiety is a sugar moiety.

The invention further provides pharmaceutical compositions for treating an α-pyrone responsive state in a mammal. The pharmaceutical compositions include a therapeutically effective amount of an α-pyrone described supra and a pharmaceutically acceptable carrier.

The present invention also provides packaged pharmaceutical compositions for treating an α-pyrone responsive state in a mammal. The packaged pharmaceutical compositions include a container holding a therapeutically effective amount of at least one α-pyrone, as described supra, and instructions for using the α-pyrone for treating an α-pyrone responsive state in the mammal.

The present invention further provides the new and useful α-pyrones having the formulae

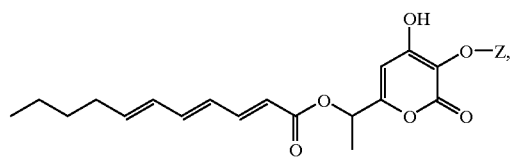

wherein Z is a sugar. Preferably, Z is either

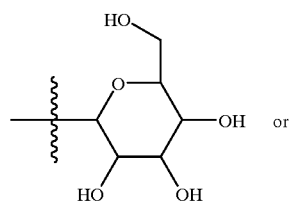

In one embodiment, the above depicted α-pyrone(s) is isolated from a fungal extract.

DETAILED DESCRIPTION

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention pertains to methods for controlling an α-pyrone responsive state in a mammal. The methods include administration of a therapeutically effective amount of an α-pyrone to the mammal, such that control of α-pyrone responsive state in the mammal occurs.

The language "α-pyrone responsive state" is intended to include a disease state or condition characterized by its responsiveness to treatment with an α-pyrone, e.g. the treatment includes a significant diminishment of at least one symptom or effect of the state achieved with an α-pyrone. Typically such states are associated with an increase of a pathogen within a host such that the host often experiences physiological symptoms which include, but are not limited to, release of toxins, gastritis, inflammation, coma, water retention, weight gain or weight loss and immunodeficiency. The effects often associated with such symptoms include, but are not limited to, fever, nausea, diarrhea, weakness, headache, and even death. In one embodiment, an α-pyrone responsive state is associated with DNA ligase joining activity. Examples of α-pyrone responsive states include undesirable cell proliferation, bacterial infection and cancer.

The language "control of an α-pyrone responsive state" or "controlling an α-pyrone responsive state" is intended to include changes in a disease state or condition, as described above, such that physiological symptoms in a mammal can be significantly diminished or minimized. The language also includes prevention or inhibition of physiological symptoms or effects associated with an aberrant cell. In one preferred embodiment, the control of the disease state or condition is such that the disease state or condition is eradicated. In another preferred embodiment, the control is selective such that a particular targeted aberrant cell is controlled while other cells which are not detrimental to the mammal are allowed to remain substantially uncontrolled or substantially unaffected, e.g., lymphocytes, red blood cells, white blood cells, platelets, growth factors, etc.

The language "undesirable cell proliferation" is intended to include abnormal growth of cells which can be detrimental to a mammal's physiological well being. Effects of undesirable cell proliferation can include the release of toxins into the mammal, fever, gastritis, inflammation, nausea, weakness, coma, headache, water retention, weight gain or weight loss, immunodeficiency, death, etc. The undesired cells which proliferate can include cells which are either benign or malignant. Examples of undesirable cell proliferation include bacterial cell proliferation and aberrant cell division and/or proliferation of foreign cells, such as in cancer cells.

The language "aberrant cell division and/or proliferation" is art recognized and is intended to cover those instances where cells are generated in excess of what is considered typical in physiologically similar environment, such as in cancers.

The language "control of undesirable cell proliferation" or "controlling undesirable cell proliferation" is intended to include changes in growth or replication of undesired cells or eradication of undesired cells, such as bacteria, cancer, or those cells associated with abnormal DNA ligase joining activity. The language includes preventing survival or inhibiting continued growth and replication of an undesired cell. In one preferred embodiment, the control of the undesired cell is such that an undesired cell is eradicated. In another preferred embodiment, the control is selective such that a particular targeted undesired cell is controlled while other cells which are not detrimental to the mammal are allowed to remain substantially uncontrolled or substantially unaffected, e.g., lymphocytes, red blood cells, white blood cells, platelets, growth factors, etc.

The term "cancer" is art recognized and is intended to include undesirable cell proliferation and/or aberrant cell growth, e.g., proliferation.

The term "α-pyrone" is art recognized and is intended to include those compounds having a formula

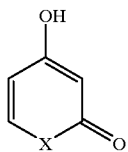

wherein X is either an oxygen, sulfur, nitrogen or phosphorous atom. An α-pyrone is also referred to as a 1,2-pyrone (2H-pyran-2-one). The α-pyrones of the invention can be substituted or unsubstituted as described infra. Suitable examples of α-pyrones which are new and useful in this invention are described infra.

The present invention also pertains to methods for controlling a bacterial infection in a mammal. The methods include administration of a therapeutically effective amount of an α-pyrone to a mammal, such that control of the bacterial infection in the mammal occurs.

The language "control of a bacterial infection" or "controlling a bacterial infection" is intended to include changes in growth or replication of undesired bacteria or eradication of bacteria. The language includes preventing survival or inhibiting continued growth and replication of undesired bacteria. In one preferred embodiment, the control of the bacteria is such that a bacteria is eradicated. In another preferred embodiment, the control is selective such that a particular targeted bacteria is controlled while other cells which are not detrimental to the mammal are allowed to remain substantially uncontrolled or substantially unaffected, e.g., lymphocytes, red blood cells, white blood cells, platelets, growth factors, etc. In another embodiment, the bacterial infection can be associated with abnormal DNA ligase joining activity.

The term "bacteria" is art recognized and is intended to include prokaryotic single celled or non cellular microorganisms traditionally classified with the fungi as Schizomycetes, and being autotrophic, saprophytic, or parasitic. Effects of undesirable bacteria can include the release of toxins into the mammal, fever, gastritis, inflammation, nausea, weakness, coma, headache, water retention, weight gain or weight loss, immunodeficiency, death, etc. Examples of suitable bacteria amenable to the diagnostic and therapeutic methods described herein include, but are not limited to, *Streptococcus albus, Bacillus sphaericus, Bacillus subtilis, Bacillus licheniformis, Streptococcus pneumoniae, Staphylococcus simulans, Staphylococcus aureus, Lactobacillus lactis, Lactobacillus delbrueckii,* Chalaropsis sp., *Streptococcus globosporus, Clostridium acetobutylicum, Enterococcus hirae, Streptococcus faecalis, Escherichia coli, Arthrobacter crystallopoietes, Bacillus cereus, Bacillus stearothermophilus, Bacillus thruingiensis, Brucella abortus, Clostridium botulinum, Clostridium welchii, Lactobacillus acidophilus, Listeria monocytogenes, Micrococcus luteus, Mycobacterium smegmatis,* Myxobacter sp., *Neisseria gonorrhoeae, Proteus vulgaris, Pseudomonas aeruginosa, Salmonella typhimurium, Streptococcus hydrocopicus, Streptococcus pyogenes, Pseudomonas fluorescens, Streptomyces griseofuscus, Enterococcus faecalis, Streptomyces roseosporus, Actinomyces utahensis, Streptomyces fradiae, Staphylococcus epidermidis, Clostridum difficile, Bacillus megaterium, Klebsiella aerogenes, Pseudomonas cocvenenans, Streptomyces cattleya, Empedobacter lactamgenus* and *Aspergillus candidus.*

The present invention further pertains to methods for treating cancer in a mammal by administering to the mammal a therapeutically effective amount of an α-pyrone, such that treatment of the cancer in the mammal occurs.

The language "treating cancer" or "treatment of cancer" is intended to include changes in growth or replication of cancer or eradication of cancer. The language includes preventing survival or inhibiting continued growth and replication of cancer. In one preferred embodiment, the control of the cancer is such that the cancer eradicated. In another preferred embodiment, the control is selective such that a particular targeted cancer is controlled while other cells which are not detrimental to the mammal are allowed to remain substantially uncontrolled or substantially unaffected, e.g., lymphocytes, red blood cells, white blood cells, platelets, growth factors, etc. In another embodiment, the cancer can be associated with abnormal DNA ligase joining activity.

The term "cancer" is art recognized and is intended to include abnormal proliferation of cells which can be detrimental to a mammal's physiological well being. Effects of cancer can include the release of toxins into the mammal, inflammation, nausea, weakness, coma, headache, water retention, weight gain or weight loss, immunodeficiency, death, etc. The cancer cells can be either benign or malignant, including proliferation of cells such that aberrant cell division and/or proliferation of the cells occurs. Examples of cancers which can be treated by the present invention include a wide variety of cell types that proliferate uncontrollably. For example, the diagnostic and therapeutic methods of the present invention can be applied to cancerous cells of mesenchymal origin, such as those producing sarcomas (e.g., fibrosarcoma, myxosarcoma, liosarcoma, chondrosarcoma, osteogenic sarcoma or chordosarcoma, angiosarcoma, endotheliosardcoma, lympangiosarcoma, synoviosarcoma or mesothelisosarcoma); leukemias and lymphomas such as granulocytic leukemia, monocytic leukemia, lymphocytic leukemia, malignant lymphoma, plasmocytoma, reticulum cell sarcoma, or Hodgkin's disease; sarcomas such as leiomysarcoma or rhabdomysarcoma, tumors of epithelial origin such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, chorioaencinoma, semonoma, or embryonal carcinoma; and tumors of the nervous system including gioma, menigoma, medulloblastoma, schwannoma or epidymoma. Additional cell types amenable to diagnosis and treatment according to the methods described herein include those giving rise to mammary carcinomas, gastrointestinal carcinoma, such as colonic carcinomas, bladder carcinoma, prostate carcinoma, and squamous cell carcinoma of the neck and head region.

The present invention pertains to methods for treating diseases characterized by aberrant DNA ligase joining activity in a mammal. The methods include administration of a therapeutically effective amount of an α-pyrone to the mammal, such that aberrant DNA ligase joining activity in the mammal is treated. The DNA ligase joining activity can be associated with undesirable cell proliferation, such as bacterial or cancer proliferation.

The language "DNA ligase joining activity" is art recognized and is intended to include activity associated with DNA replication, repair, and recombination by joining single and double stranded DNA with formation of phosphodiester bonds.

The language "treating DNA ligase joining activity" or "DNA ligase joining is treated" is intended to include changes in the activity associated with DNA replication, repair, and recombination by joining single and double stranded DNA with formation of phosphodiester bonds. In a preferred embodiment, treatment of aberrant DNA ligase joining activity is such that aberrant DNA ligase joining activity is controlled, e.g., prevented or inhibited. In a preferred embodiment, treatment is selective such that a particular target cell associated with the DNA ligase joining activity is treated while other cells not detrimental to the mammal are allowed to remain substantially untreated or substantially unaffected, e.g., lymphocytes, red blood cells, white blood cells, platelets, growth factors, etc.

The language "therapeutically effective amount" of an α-pyrone, described infra, is that amount of a therapeutic compound necessary or sufficient to perform its intended function within a mammal, e.g., treat an α-pyrone responsive state, undesirable cell proliferation, undesirable bacteria proliferation, cancer, or DNA ligase joining activity in a mammal. An effective amount of the therapeutic compound can vary according to factors such as the amount of the causative agent already present in the mammal, the age, sex, and weight of the mammal, and the ability of the therapeutic compounds of the present invention to affect an α-pyrone responsive state in the mammal. One of ordinary skill in the art would be able to study the aforementioned factors and make a determination regarding the effective amount of the therapeutic compound without undue experimentation. An in vitro or in vivo assay also can be used to determine an "effective amount" of the therapeutic compounds described infra. The ordinarily skilled artisan would select an appropriate amount of the therapeutic compound for use in the aforementioned assay or as a therapeutic treatment.

A therapeutically effective amount preferably diminishes at least one symptom or effect associated with the α-pyrone responsive state being treated by at least about 20%, more preferably by at least about 40%, even more preferably by at least about 60%, and still more preferably by at least about 80% relative to untreated subjects. Assays can be designed by one skilled in the art to measure the diminishment of such symptoms and/or effects. Any art recognized assay capable of measuring such parameters are intended to be included as part of this invention. For example, if cancer is the state being treated, then the size of a tumor can be measured before and after treatment for measurement of diminishment in its size using an art recognized technique.

The term "mammal" is art recognized and is intended to include an animal, more preferably a warm-blooded animal, most preferably cattle, sheep, pigs, horses, dogs, cats, rats, mice, and humans. Mammals susceptible an α-pyrone responsive state, undesirable cell proliferation, DNA ligase joining activity, bacterial infection or cancer are included as part of this invention.

The present invention pertains to compounds, α-pyrones, having the formula

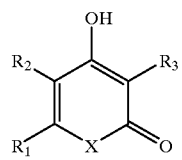

and pharmaceutically acceptable salts or esters and esters thereof. X is O, S, N or P. $R_1$ or $R_2$ are each independently a hydrogen atom or a cell penetrating moiety and $R_3$ is a solubilizing moiety. Preferably, $R_1$ is a cell penetrating moiety, such as a substituted or unsubstituted alkyl ester group and $R_3$ is a solubilizing moiety, such as a sugar.

The language "cell penetrating moiety" is intended to include those organic and/or inorganic functional groups which facilitate entry of a compound of the invention into a cell, e.g., by penetration or crossing of the cell membrane, the cell wall, lipopolysaccharides, mucopolysaccharides and/or cell surface active agents associated with cellular physiology via diffusion, mass transport, active transport and the like. Cell penetrating moieties include, but are not limited to, lipophilic and hydrophobic solubilizers. Suitable examples of cell penetrating moieties include substituted or unsubstituted alkyl ester groups, alkenyl ester groups, alkynyl ester groups and substituted and unsubstituted alkyl groups.

The terms "alkyl ester group", "alkenyl ester group" and "alkynyl ester group" are art recognized and are intended to include those ester groups including an alkyl, alkenyl or alkynyl group, respectively, e.g., a carbon atom side chain as described infra.

The term "lipophilic" is art recognized and is intended to include those organic and/or inorganic functional groups which describe those compounds which are more soluble in nonpolar solvents, e.g., chloroform, ethers, than in water. Suitable examples of lipophilic solubilizers include fats, waxes, phosphoglycerides, cerebrosides, substituted or unsubstituted alkyl, alkenyl or alkynyl ester groups, substituted or unsubstituted alkyl, alkenyl, or alkynyl groups, etc. The lipophilic substances encompassed by this invention include unsaturated fatty acids such as linoleic acid, linolenic acid, oleic acid, arachidonic acid and erucic acid and their glycerides, saturated fatty acids such as palmitic acid and stearic acid and their glycerides, and lipophilic vitamins such as vitamins A, D and E. Different techniques concerned with solubilizing lipophilic compounds include those described by Praveen et al., U.S. Pat. No. 5,314,685, and Fernandes et al., U.S. Pat. No. 4,992,271.

The term "hydrophobic" is art recognized and is intended to include those organic and/or inorganic functional groups which describe those compounds which are more soluble in hydrocarbon solvents, e.g. octane, dodecane, and are substantially insoluble in water at 25° C. Suitable examples of hydrophobic groups include substituted or unsubstituted alkyl, alkenyl, or alkynyl groups and substituted and unsubstituted alkyl, alkenyl, or alkynyl ester groups. Functionality that can be associated with hydrophobic groups include halogen atoms, preferably chloride or flouride, aromatic groups, such as phenyl, naphthyl, etc. or silicon containing groups such as, for example, compounds derivatized with hexamethyldisilazane, hexamethyldisiloxane, trimethylchlorosilane, trimethylmethoxysilane, trimethylethoxysilane, triethylethoxysilane, triethylmethoxysilane, dimethyldichlorosilane, dimethyldiethoxysilane, methyltrichlorosilane, and ethyltrichlorosilane, etc.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)).

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure, even more preferably one to three carbon atoms in its backbone structure. Likewise, "lower alkenyl" and "lower alkynyl" have similar chain lengths.

The terms "alkoxyalkyl", "polyaminoalkyl" and "thioalkoxyalkyl" refer to alkyl groups, as described above, which further include oxygen, nitrogen or sulfur atoms replacing one or more carbons of the hydrocarbon backbone, e.g., catenary oxygen, nitrogen or sulfur atoms.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" as used herein means an atom of any element other than carbon or hydrogen. Preferred heteroatoms are nitrogen, oxygen, sulfur and phosphorus.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis.

In one embodiment, the hydrophobic moiety is an alkyl ester group having the formula

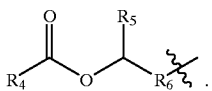

$R_4$ is a substituted or unsubstituted alkyl or alkenyl group, preferably an alkenyl group having a carbon atom chain of between six and twelve carbon atoms. $R_5$ is a hydrogen atom or a substituted or unsubstituted alkyl or alkenyl group, preferably a methyl group. $R_6$ is a substituted or unsubstituted alkyl or alkenyl group or a covalent bond, preferably a covalent bond to the α-pyrone ring. In a preferred embodiment, X is O, $R_4$ is an alkenyl group,

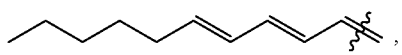

$R_5$ is a methyl group and $R_6$ is a covalent bond, e.g.,

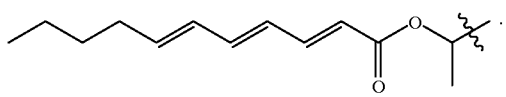

The language "solubilizing moiety" is intended to include those organic and/or inorganic functional groups which help to solubilize the compound in an aqueous or polar environment, such as at a normal cell physiological pH. Solubilizing moieties include, but are not limited to, hydrophilic moieties. Suitable examples of solubilizing moieties include polyalkylene oxides, polyamines, alkoxyesters, amides, sugars, etc.

The term "hydrophilic" is art recognized and is intended to include those organic and/or inorganic functional groups which are more soluble in water than in nonpolar or hydrocarbon solvents. Suitable examples of hydrophilic moieties include alkoxides, such as phenols, hydroxybiphenyls, polyalkylene oxides (polyethers), polyamines, biphenyls and sugars. In a preferred embodiment, the hydrophilic moiety is a sugar, such as glucose or any hexose.

The term "polyalkylene oxide" is art recognized and is intended to include groups having a repeat unit of $(R_1—O—R_2)_n$, wherein $R_1$ and $R_2$ can be the same or different and wherein n is a positive integer between about 2 and 10,000, inclusive. Typically such groups are derived from condensation reactions between two or more molecules of cyclic ethers or linear diols. Furthermore, the polyalkylene oxide can terminate in either an alkyl group or a hydroxyl group. The molecular weight of the polyalkylene oxide will depend mainly upon the end use of the derivatized α-pyrone. Those of ordinary skill in the art are capable of determining molecular weight ranges suitable for end-use applications. In general, the useful range of molecular weight is a number average molecular weight between about 600 and about 100,000 daltons, and preferably between about 2,000 and about 20,000 daltons. Suitable examples of polyalkylene oxides include polyethylene, polypropylene and polybutylene oxides having molecular weights of 50 to 10,000, inclusive.

The term "polyamine" is art recognized and is intended to include groups having a repeat unit of $(R_1—NR_2R_3—)_n$, wherein $R_1$ and $R_2$ can be the same or different, wherein $R_3$ can be an alkyl substituent or a hydrogen and wherein n is a positive integer between about 2 and 10,000, inclusive. Typically, such groups are derived from condensation reactions between two or more molecules of cyclic amines or linear amines. Furthermore, the polyamine can terminate in either as an alkyl group or a hydrogen. The molecular weight of the polyamine will depend mainly upon the end use of the derivatized α-pyrone. Those of ordinary skill in the art are capable of determining molecular weight ranges suitable for end-use applications. In general, the useful range of molecular weight is a number average molecular weight between about 600 and about 100,000 daltons, and preferably between about 2,000 and about 20,000 daltons. Suitable examples of polyamines include polyethyleneamine, polypropyleneamine, polybutyleneamine, etc.

The term "alkoxyester" is art recognized and is intended to include those groups depicted by the formulae —$(R_1—O—R_2)_n$—C(O)—R or —C(O)—$(R_1—O—R_2)_n$ wherein $(R_1—O—R_2)_n$ is as described for polyalkylene oxides and wherein the point of attachment to an α-pyrone can be either a carbon radical or a hydroxide radical.

The term "aminoester" is intended to include those group depicted by the formulae —$(R_1—NR_2R_3—)_n$—C(O)—R or —C(O)—$(R_1—NR_2R_3—)_n$ wherein $(R_1—NR_2R_3—)_n$ is as described for polyamines and wherein the point of attachment to an α-pyrone can be either a carbon radical or a hydroxide radical.

The term "sugar" is art recognized and is intended to include those carbohydrates having up to and including eight saccharide units. Suitable examples include monosaccharides, e.g., pentoses, hexoses, disaccharides, e.g. sucrose, lactose, maltose, melibiose, cellobiose, trehalose and trisaccharides, e.g. raffinose. It is to be understood that sugars are optically active and all optically active forms of sugars are included in the present invention.

In a most preferred embodiment, the present invention includes a compound having the formula

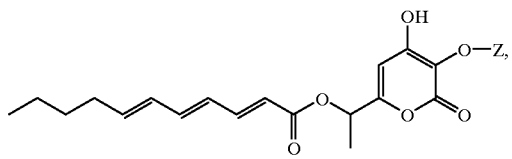

wherein Z is a sugar. Preferably, Z is either

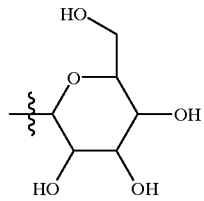

or

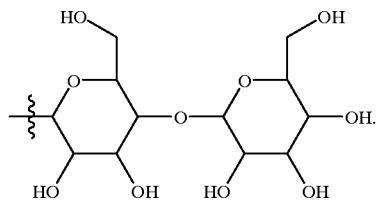

In certain embodiments, the compounds of the invention have the formula

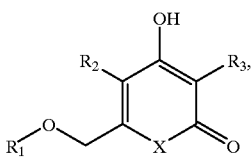

wherein $R_1$, $R_2$ and $R_3$ are as defined supra. Preferably, $R_1$ includes an alkenyl group attached to a carbonyl. In other embodiments, the compounds of the invention have the formula

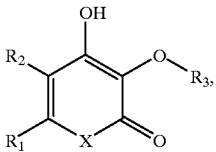

wherein $R_1$, $R_2$ and $R_3$ are as defined supra. Preferably $R_3$ includes a sugar moiety, a carbonyl group, a polyalkylamine or a polyalkyloxide.

In certain embodiments, compounds of the invention have the formula

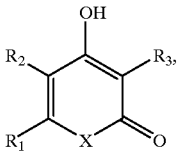

wherein $R_3$ includes ring containing moieties as described supra. In other embodiments, $R_2$ of the compounds of the invention cannot be hydrogen. In additional embodiments, $R_1$ and $R_3$ both have moieties which contain greater than ten carbon atoms, more preferably fifteen or more carbon atoms. In yet other embodiments, neither $R_2$ or $R_3$ are hydrogen or lower alkyl groups.

In certain embodiments, α-pyrone compounds are not inhibitors of human leucocyte elastase such as those compounds described in WO 88/10258, the contents of which are expressly incorporated herein by reference. In another embodiment, the α-pyrone compound differs from the species of the α-pyrone compounds described in WO 88/10258.

In another embodiment, the α-pyrone responsive state does not include tumor growth.

The invention further provides pharmaceutical compositions for treating an α-pyrone responsive state, e.g., undesirable cell proliferation in a mammal. The pharmaceutical compositions include a therapeutically effective amount of α-pyrones described supra and a pharmaceutically acceptable carrier.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can performs its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As set out above, certain embodiments of the present compounds can contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1–19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. Hydroxyls can be converted into esters via treatment with an esterifying agent such as alkanoyl halides. The term is further intended to include lower hydrocarbon groups capable of being solvated under physiological conditions, e.g., alkyl esters, methyl, ethyl and propyl esters. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 0.1 to about 40 mg per kg per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

The present invention also pertains to packaged pharmaceutical compositions for treating an α-pyrone responsive state, e.g., undesirable cell proliferation in a mammal. The packaged pharmaceutical compositions include a container holding a therapeutically effective amount of at least one α-pyrone as described supra and instructions for using the α-pyrone for treating the α-pyrone responsive state in the mammal.

The present invention further provides methods of isolating or preparing an α-pyrone having the formula

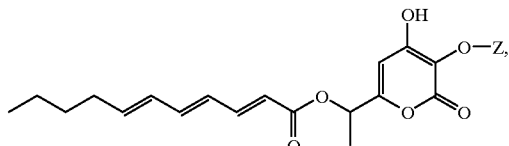

wherein Z is a sugar, preferably

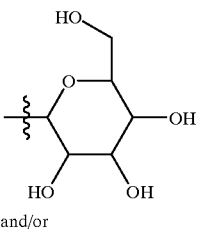

and/or

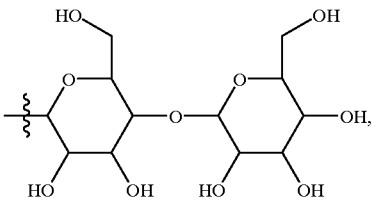

from an extract of AA11186 from Fusarium, isolated from asparagus in Bukit Temiang, Malaysia. The isolation includes the steps of described in the exemplification.

Alternatively, the compounds of the invention, including the compound isolated from the extract depicted above, can be prepared by using chemical synthetic techniques which are art recognized and/or are described below included in the exemplifications.

Compounds of the general formula

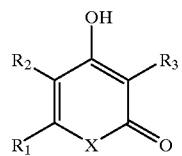

can be prepared by reacting an appropriate acid imidazolide with an appropriate salt of an alkyl hydrogen malonate to form the corresponding 3-oxocarboxylate ester (B. Ternai el al. PCT/AU88/00155). Hydrolysis of the 3-oxocarboxylate ester to afford the corresponding 3-oxocarboxylic acid followed by cyclization of the 3-oxocarboxylic acid with carbonyl-diimidazole affords the corresponding 3-(1'-oxo-alkyl)-4-hydroxy-6-alkyl-2-pyrones of the above formula wherein $R_1$, $R_2$ and $R_3$ are as described supra. Additionally, alkylation of the above formula can be prepared by reaction of 3-(1'-oxo-alkyl)-4 hydroxy-6-methyl-2-pyrone with alkylating agents as described by G. R. Poulton and T. D Cyr, *Can. J. Chem.* 1980, 58, 2158–2160 and W. C. Groutas et al., *J. Med. Chem.* 1985, 28, 1106–1109.

Alternatively, 2-pyrones modified at the C3 position can be prepared by synthetic modifications of

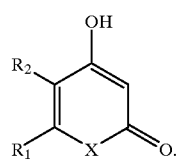

Treatment of an appropriately protected pyrone followed by reaction with an electrophilic reagent can be used to fanctionalize the C3 site (G. R. Poulton, supra). Further modifications by hydrolysis, hydrogenation, Wittig type couplings and oxidation reactions are known to those skilled in the art and modifications can be made to the 2-pyrones under standard synthetic conditions. Conversion of a 2-pyrone, wherein X is oxygen, can be accomplished by treatment with an appropriate reagent, such as ammonia, or other suitable nucleophilic reagents to obtain the desired derivatized pyrone (C.-S. Wang *J Heterocycl. Chem*. 1970, 7, 389–392).

The invention is further illustrated by the following examples which in no way should be construed as being further limiting. The contents of all references, cited throughout this application are hereby incorporated by reference.

EXEMPLIFICATION

α-Pyrones Inhibit DNA Ligase Joining Activity
DNA Ligase Assay

The assay described below was designed to monitor the activity of the essential DNA Ligase. The enzyme catalyses the formnation of a covalent phosphodiester bond between juxtaposed 5' phosphate and 3' hydroxyl termini in duplex DNA containing a single-strand break. The activity requires NAD+ and involves a lysyl-AMP intermediate. The assay involved the addition of a short double-stranded DNA substrate containing a single-strand break into methanol-solubilized extract wells. The enzyme and a buffer were added; following incubation, activity was monitored using streptavidin binding and fluorescence detection of the covalently joined substrate. Inhibition of DNA ligation resulted in a reduction of fluorescent signal.

REAGENTS LIST

50% Methanol (1:1 ratio of Methanol (Fisher HPLC grade) and sterile Milli-Q water was prepared and stored at room temperature (25° C.).
1 M Tris-HCl The solution was prepared with autoclaved Milli-Q water, the pH adjusted to 7.8 with 10N NaOH, filtered through a 0.2 μM filter (Sterilized) and stored room temperature (25° C.).
10 mM Tris-HCl The solution was prepared as a 100× dilution from 1M Stock 1M Tris-HCl solution, pH 7.8, with sterile Milli-Q water and stored at room temperature (25° C.).
5× *E. coli* Ligase Reaction Buffer The buffer was prepared with 150 mM Tris-HCl (pH 7.8 from 1M stock), 5 mM Dithiothritol (Boehringer Mannheim), 20 mM $MgCl_2$ (1M Stock), 130 μM NAD+(Sigma) and 250 μg/ml acetylated BSA (Sigma). The solution was stored as aliquots at −20° C.
*E. coli* DNA Ligase Enzyme *E. coli* DNA ligase enzyme was used as received from New England Biolabs supplied at 10 U per μl. Samples were stored at −20° C.
Ligase Stop Solution Ligase stop solution was prepared with 2× SSC (sodium chloride, sodium citrate) (from 20× Sigma), 150 mM Tris-Cl (from 1M, pH 7.8 stock), 50 mM EDTA (from 0.5 M, pH 8.0 stock) and the pH adjusted to 6.8 with 12N HCl. The solution was stored at room temperature (25° C.).
Alk/SDS The Alk/SDS Wash was prepared from 50 mM NaOH, 0.1% SDS. (Prepared from 10N NaOH stock, sterile Milli-Q water and 10% SDS filtered stock.) The buffer was stored at room temperature (25° C.) and used within 2 weeks of preparation.
Streptavidin-coated Microtiter Plates (transparent) were used as supplied by Boehringer Mannheim Corporation (#1734776).

SUBSTRATE OLIGONUCLEOTIDES
Fluorescein Oligo (aka F-oligo)

Fluorescein Oligo was synthesized at 1 μM, purified by HPLC column and diluted to 1 nMole/μl concentrated stock with sterile Milli-Q water. The solution was stored at −20° C. and diluted with sterile Milli-Q water to 0.1 nMole/μl for working solutions which were stored at −20° C.

5' FITC-GAATACGTGACCTTGACCTAG 3'
Scaffold Oligo (aka S-oligo)

The scaffold Oligo was synthesized at 1 μM, diluted to 1 nMole/μl concentrated stock with sterile Milli-Q water and stored at −20° C. The solution was diluted with sterile Milli-Q water to 0.1 nMole/μl for working solutions and stored at −20° C.

5' ACATGCACTTCAGTCATGAGCCTAGGT-CAAGGTCACGTATTC 3'
Biotin Olipo (aka B-oligo)

Biotin Oligo was synthesized at 1 μM, diluted to 1 nMole/μl concentrated stock with sterile Milli-Q water and stored at −20° C. The solution was diluted with sterile illi-Q water to 0.1 nMole/μl for working solutions and was stored at −20° C.

5' PO4-GCTCATGACTGAAGTGCATGTTT-biotin 3'
Prepare Substrate Solution (40 μl/AP) were prepared in advance and stored as liquots at −20° C. for months.

Use 0.1 nMole/μl dilutions of F-oligo, B-oligo and S-oligo
Per ml of substrate solution:
3 μl F-oligo
3 μl B-oligo
6 μl S-oligo
up to 1 ml with 10 mM Tris-Cl (pH 7.8)

Place in boiling water bath, 10 min., remove to ice at least 15 min or −20° for long term storage.

METHOD

Assay Assembly

Individual assays were run in a total volume of 100μl. 1 hour before beginning the assay, sufficient 5× *E. coli* Ligase Reaction Buffer and Substrate Solution was removed from −20° C. and allowed to thaw at room temperature (25° C.). The enzyme was added to the 5× *E. coli* Ligase Reaction Buffer just prior to use.

Contents of the wells were solubilized with 40 μl 50% Methanol Solution using a Matrix Impact 8-channel pipettor as a dispenser. 40 μl of Substrate Solution was added to each well with the Matrix Impact 8-channel pipettor as a dispenser. 20 μl of 5× *E. coli* Ligase Reaction Buffer containing 0.5 U *E. coli* DNA Ligase enzyme was added (to each well using a 12 channel pipetman (0–50 microliters). The contents of the wells were mixed by gently shaking plate.

The samples were incubated for 90 minutes at room temperature (25° C.). The reaction was stopped by the addition of 100 μl of Ligase Stop Solution to each well with thorough mixing. 160μl of the stopped reaction was transferred to Streptavidin microtiter plates for binding over 4 hours at room temperature (25° C.) or 4° C. overnight.

The liquid was aspirated from the streptavidin plates, the plates were rinsed 2× with Milli-Q water and aspirated. 200 μl of Alk/SDS Wash was added to each plate, incubated for 30 min at room temp and aspirated. The wells were rinsed with Milli-Q water, treated with 200 μl Alk/SDS Wash and the Fluorescence 485/530 was determined on Cytofluor (use Gain=90).

Primary Screen

A natural product fungal library was screened for biological activity by preparing butanol extracts from a broth containing fungi of interest. In this manner, hundreds of natural products were examined for activity. The screening process used for this purpose is described below:

A fungal culture was revived from frozen stock in 6 ml of potato dextrose broth ((2.24% Potato Dextrose, 0.1% yeast extract (pH to 6.0)). After 3 days, a 125 ml shake flask containing 50 ml mixed malt media ((2% malt extract, 2% dextrose, 1% cracked malt, 0.1% peptone (no pH adjustment)) was inoculated and grown at 30° C., 250 rpm for 1 week. For example, a fungal culture of AA11186, described infra, was screened along with hundreds of other fungal samples using the assay procedure described above.

An equal volume of broth and butanol (15 mL/15 mL) were combined and mixed vigorously on a shaker for 3 minutes. The sample was spun down at 4200 rpm for eight minutes at room temperature (25° C.) and the top layer was extracted.

A 100 μl sample of butanol extract of broth was evaporated into a 96 well plate.

Additional samples of 50 μl, 25 μl, 12.5 μl and 6.25 μl were added to individual wells. To each well was then added 3 μl F-oligo, 3 μl B-oligo, 6 μl S-oligo as described above. Samples were then tested for fluorescence. Inhibition by a compound of the invention was noted by the loss of fluorescence by the sample. Fluorescence indicated lack of inhibition and enzymatic action.

|  | Fluorescence (Units) | |
| --- | --- | --- |
| Dilution | 11186 Sample | Control (no 11186) |
| 100 μl | 1245 | 1281 |
| 50 μl | 1277 | 1295 |
| 25 μl | 1482 | 1355 |
| 12.5 μl | 1740 | 1284 |
| 6.25 μl | 2203 | 1355 |

The results indicate that as the amount of enzyme inhibitor, 11186, an α-pyrone, is diluted, the enzyme is still active and that at a dilutions of 25 μl to 100 μl, significant inhibition of enzymatic activity occurs. These results also indicate that control of undesired cell proliferation, control of undesired bacteria, treatment of cancer and control of DNA ligase joining activity can be affected by the use of α-pyrones. Samples which demonstrated inhibition were then scaled up and grown for a secondary screening.

Isolation of DNA Ligase Inhibitor 11186

A fungal strain designated as AA11186, identified as a Fusarium, was isolated from asparagus in Bukit Temiang, Malaysia. Fusarium have a complicated taxonomy and are identified based on colonial morphology involving the size and curvature of the macroconidia and the relative length of foot cells. Typically, classification approaches are based on results of crosses with tester strains; a successful cross is one that produces "copious" numbers of ascospores. AA11186 did not cross with any of the testers and was therefore identified as mating population X.

The culture was revived from frozen stock in 6 ml of potato dextrose broth ((2.24% Potato Dextrose, 0.1% yeast extract (pH to 6.0)). After 3 days, a 125 ml shake flask containing 50 ml mixed malt media ((2% malt extract, 2% dextrose, 1% cracked malt, 0.1% peptone (no pH adjustment)) was inoculated and grown at 30° C., 250 rpm for 3 days. The 50 ml seed culture was inoculated into a two liter shake flask containing one liter mixed malt media. The broth was harvested after 6 days of stirring at 250 rpm at 30° C.

The fermentation broth of AA11186 was separated into mycelium and supernatant. The supernatant was extracted twice with equal volumes of ethyl acetate and the mycelium was extracted twice with methanol. The ethyl acetate layer of the supernatant and the methanol extract of the mycelium were dried and combined to give 476 mg of crude extract. About 300 mg of the extract was separated by C18 HPLC under the following conditions: HPLC column, Dynamax C18, 5 μm, 22×250 mm with a guard column; Solvent A (5% methanol/water); Solvent B (100% methanol); gradient 0–8 minutes 100% solvent A; 8–40 minutes 100% solvent A to 100% solvent B; 40–56 minutes 100% solvent B; flow rate 8 ml/minute; fraction size 4 ml/fraction. DNA ligase inhibitory compounds were eluted in mostly in fractions 78 and 79. The combined fractions afforded 6.2 mg of a material, 11186, identified as α-pyrones having the formulae

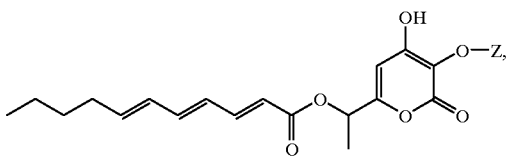

wherein Z is the sugar,

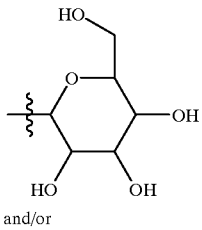

and/or

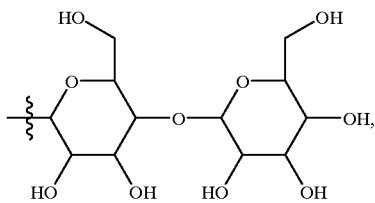

characterized by $^{13}$C NMR (nuclear magnetic resonance), $^1$H NMR, UV-VIS and mass spectral analyses.

| $^1$H NMR Spectral Data of 11186-A and 11186-B | | | |
| --- | --- | --- | --- |
| Signal # | δ | multiplicity, J (Hz) | # of protons |
| | | 1186-monoglycoside | |
| 1 | 7.40 | d, 15.5 | 1 |
| 2 | 6.49 | m | 1 |
| 3 | 6.47 | m | 1 |
| 4 | 6.05 | m | 1 |
| 5 | 6.00 | s | 1 |
| 6 | 5.91 | d, 15.5 | 1 |
| 7 | 5.58 | q, 7.0 | 1 |
| 8 | 4.39 | d, 8.0 | 1 |
| 9 | 3.84 | dd, 8.0, 12.0 | 1 |
| 10 | 3.76 | m | 1 |
| 11 | 3.70 | m | 1 |
| 12 | 3.66 | m | 1 |
| 13 | 3.56 | dd, 3.5, 7.0 | 1 |
| 14 | 3.50 | dd, 3.5, 10.0 | 1 |
| 15 | 2.22 | q, 7.5 | 2 |
| 16 | 1.9 | s | 3 |
| 17 | 1.52 | d, 6.5 | 3 |
| 18 | 1.45 | m | 2 |
| 19 | 1.35 | m | 6 |
| 20 | 0.92 | t, 6.5 | 3 |

-continued

¹H NMR Spectral Data of 11186-A and 11186-B

| Signal # | δ | multiplicity, J (Hz) | # of protons |
|---|---|---|---|
| | | 1186-diglycoside | |
| 1 | 7.40 | d, 15.5 | 1 |
| 2 | 6.49 | m | 1 |
| 3 | 6.46 | m | 1 |
| 4 | 6.22 | s | 1 |
| 5 | 6.04 | m | 1 |
| 6 | 5.91 | d, 15.5 | 1 |
| 7 | 5.63 | q, 7.0 | 1 |
| 8 | 4.55–4.83 | m | 1 |
| 9 | 3.84 | m | 1 |
| 10 | 3.79 | m | 1 |
| 11 | 3.50–3.75 | m | 4 |
| 12 | 3.40 | m | 3 |
| 13 | 3.30 | m | 3 |
| 14 | 2.22 | q, 7.5 | 2 |
| 15 | 1.90 | s | 3 |
| 16 | 1.52 | d, 6.5 | 3 |
| 17 | 1.45 | m | 2 |
| 18 | 1.33 | m | 6 |
| 19 | 0.92 | t, 6.5 | 3 |

PREPARATION OF EXEMPLARY COMPOUNDS

Sythesis of $RCOCH_2COOC_2H_5$

Solid magnesium methoxide (0.4 g, 5 mmol) is added to a solution of ethyl hydrogen malonate (1.2 g, 10 mmol) in THF and is stirred for 1 h. The solvent is removed under reduced pressure to give a white slightly hygroscopic salt, Mg (OOCOCH$_2$COOEt), which is used directly. Carbonyldiimidazole is added to a solution of carboxylic acid (10 mmol) in THF. After stirring at room temperature for six hours the prepared Mg (OOCH$_2$COOEt)$_2$ is added. The mixture is stirred for 18 h at 25° C. and the solvent is removed at reduced pressure. The residue is partitioned between ether and aq. 0.5 M HCl. The ether extract is washed with aqueous saturated. NaHCO$_3$, dried (Na$_2$SO$_4$) and concentrated under reduced pressure to yield the product.

Synthesis of $RCOCH_2COOH$

The crude ester is stirred with 1 eq. 1M NaOH overnight. Any remaining ester is removed by washing with ether. The aqueous layer is cooled and acidified with 32% HCl. The precipitated product is collected and thoroughly dried before being used in the next step. Further purification is not necessary.

Synthesis of 3-(1'oxoalkyl)-4-hydroxy-6-alkyl-2-pyrone

Solid carbonyidiimidazole is added to a THF solution of the 3-oxocarboxylic acid. The reaction is stirred under N$_2$ for 24 h, then acidified to pH 1 with 0.5M HCl. The reaction mixture is extracted with ethylacetate, the organic layer is washed with brine, dried (NaSO$_4$) and concentrated under reduced pressure to yield the desired 2-pyrone.

Equlvalents

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A compound having the formula

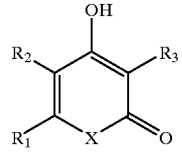

wherein

X is O or S;

$R_1$ or $R_2$ are each independently a hydrogen atom or substituted or unsubstituted alkyl ester group, alkenyl ester group or alkynyl ester group;

$R_3$ is a sugar moiety; and pharmaceutically acceptable salts or esters therof, wherein each substituent on $R_1$ and $R_2$ are each independently halogen, hydroxyl, alkylcarbonyloxy, arylcarbonyloxy, alkoxycarbonyloxy, aryloxycarbonyl, carboxylate, alkylcarbonyl, alkoxycarbonyl, aminocarbonyl, alkylthiocarbonyl, alkoxyl, phosphate, phosphonato, phosphinato, cyano, amino, alkyl amino, dialkylamino, arylamino, diarylamino, alkylarylamino, acylamino, alkylcarbonylamino, arylcarbonylamino, carbamoyl, uriedo, amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, aromatic, or heteroaromatic moieties.

2. The compound of claim 1, wherein $R_1$ is a substituted or unsubstituted alkyl ester group, alkenyl ester group, or alkynyl ester group, $R_2$ is a hydrogen atom and $R_3$ is a sugar moiety.

3. The compound of claim 2, wherein $R_1$ is a substituted or unsubstituted alkyl ester group.

4. The compound of claim 3, wherein said alkyl ester group is

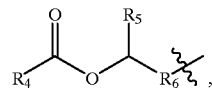

wherein $R_4$ is a substituted or unsubstituted alkyl or alkenyl group, $R_5$ is a hydrogen atom or a substituted or unsubstituted alkyl or alkenyl group, $R_6$ is a substituted or unsubstituted alkyl or alkenyl group or a covalent bond.

5. The compound of claim 4, wherein X is O, $R_4$ is

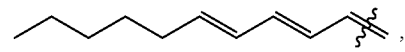

$R_5$ is a methyl group, $R_6$ is a covalent bond and $R_3$ is a sugar moiety.

6. An α-pyrone having the formula
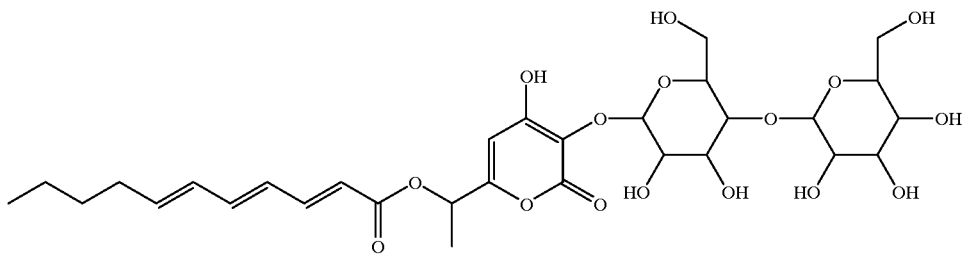
7. An α-pyrone having the formula
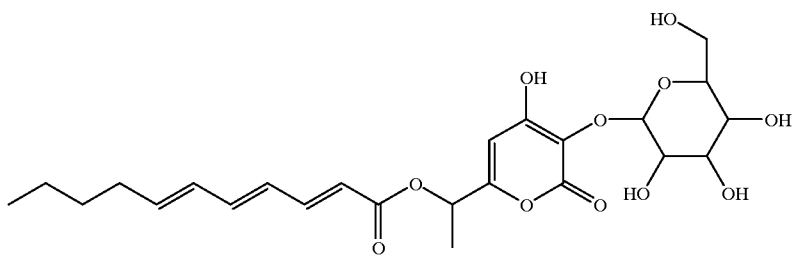
8. A pharmaceutical composition comprising a therapeutically effective amount of a compound of any one of claims 1–7 and a pharmaceutically acceptable carrier.
* * * * *